(12) United States Patent
Baska

(10) Patent No.: US 6,368,290 B1
(45) Date of Patent: Apr. 9, 2002

(54) DISPOSABLE ENDOSCOPIC BIOPSY DEVICE

(76) Inventor: Kanag Baska, 61 Woodside Avenue, Strathfield, NSW 2113 (AU)

( * ) Notice: Subject to any disclaimer, the term of this patent is extended or adjusted under 35 U.S.C. 154(b) by 0 days.

(21) Appl. No.: 09/486,927

(22) PCT Filed: Jul. 5, 1999

(86) PCT No.: PCT/AU99/00543

§ 371 Date: May 2, 2000

§ 102(e) Date: May 2, 2000

(87) PCT Pub. No.: WO00/01304

PCT Pub. Date: Jan. 13, 2000

(30) Foreign Application Priority Data

Jul. 3, 1998 (AU) .............................................. PP 4469

(51) Int. Cl.[7] .............................................. A61B 10/00
(52) U.S. Cl. ..................................................... 600/564
(58) Field of Search ................................. 600/564, 562; 606/206, 207

(56) References Cited

U.S. PATENT DOCUMENTS 5,052,402 A * 10/1991 Bencini et al. ............. 600/564
5,172,700 A * 12/1992 Bencini et al. ............. 600/564

* cited by examiner

Primary Examiner—Robert L. Nasser
Assistant Examiner—Brian Szmal
(74) Attorney, Agent, or Firm—Reising, Ethington, Barnes, Kissell, Learman & McCulloch, P.C.

(57) ABSTRACT

A biopsy device has a pair of jaws pivotally coupled for movements toward and away from one another about an axis, the jaws occupying positions on opposite sides of a plane passing between the jaws and through the axis. Each jaw has an actuating arm including an integral flexible joint operable to transmit rocking forces to the respective jaws in a selected one of two opposite directions.

11 Claims, 3 Drawing Sheets

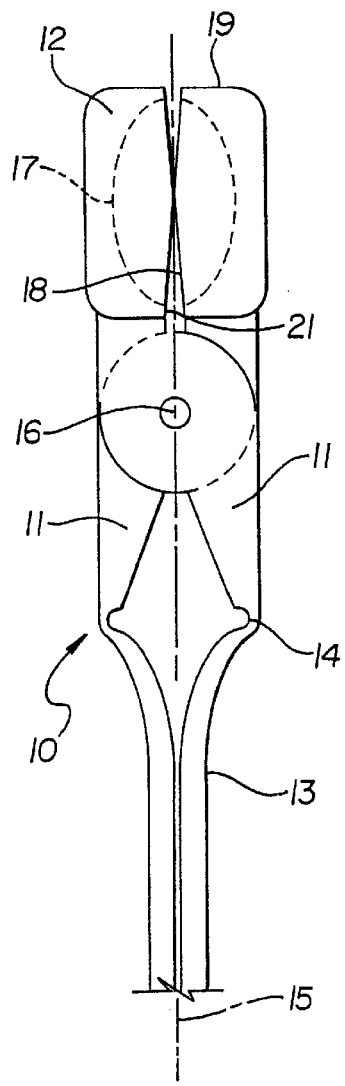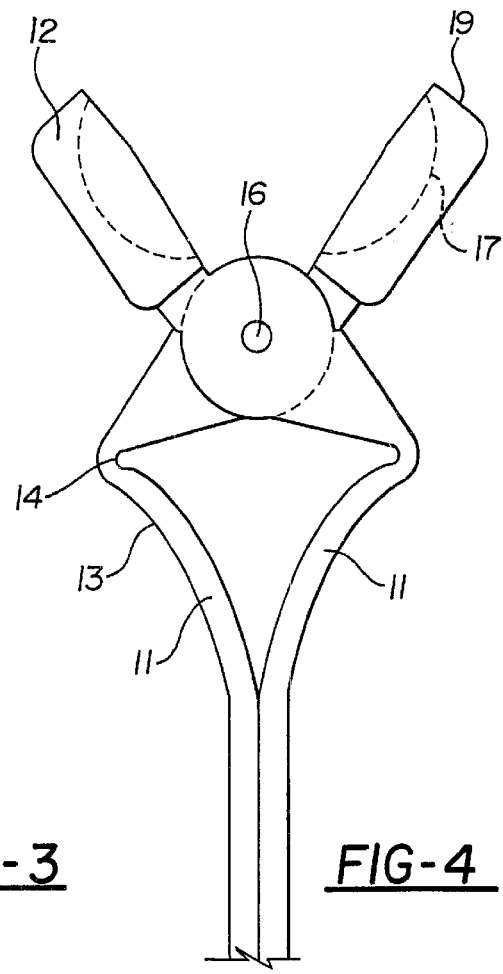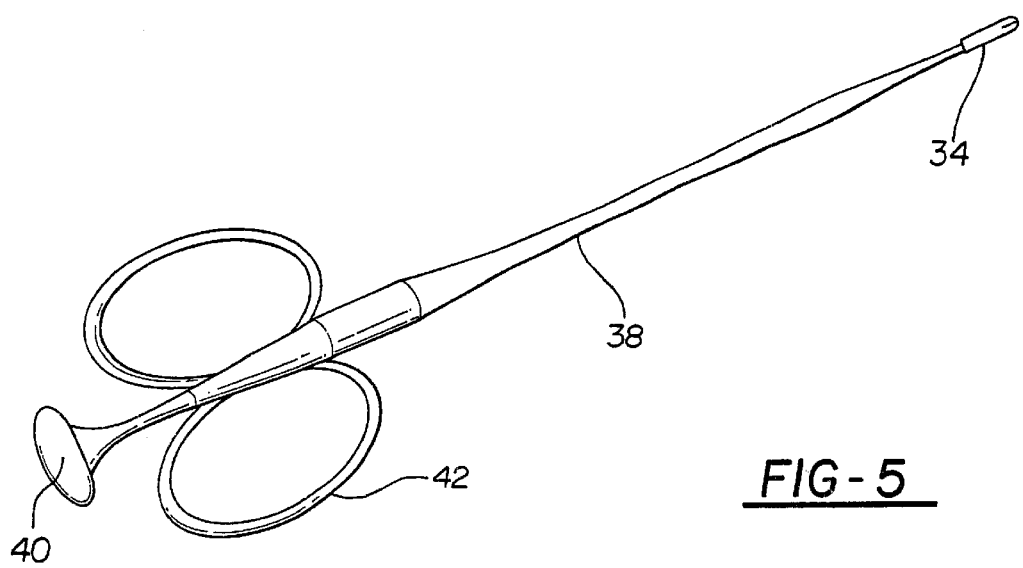
FIG-3
FIG-4
FIG-5

DISPOSABLE ENDOSCOPIC BIOPSY DEVICE

FIELD OF THE INVENTION

The present invention relates to biopsy forceps for attachment to an endoscopic biopsy device and more particularly to forceps that are inexpensive to produce and therefore disposable after one use.

BACKGROUND ART

The diagnosis of several diseases often involves the removal of small samples of tissue from a part of the living body for microscopic examination, a procedure known as biopsy. Endoscopic biopsy involves the removal of mucosal tissue or biopsy of neoplastic growths found in pans of the body accessible to an endoscope such as the gastro-intestinal tract or other parts of the body.

The endoscope is inserted into the body of an individual and when the biopsy head is adjacent an area of tissue to be sampled, it is actuated to bring two biopsy cups together. The cups act together to cut a small sample from the adjacent tissue.

The biopsy heads currently in use are usually formed of stainless steel and comprise a number of different pans which are usually hingedly joined together. As a result conventionally employed biopsy heads are expensive to make and therefore designed to be re-used many times. While the heads can be sterilised by autoclaving there is still a chance of cross contamination from one patient to another, and in particular there is justifiable concern among many that viruses such as Hepatitis B and HIV may be spread from one patient to another. It Is therefore desirable to move to a disposable alternative.

The present invention relates to a design for a biopsy forceps head which because its components need not be hingedly connected and because it may be made from a suitable synthetic plastics material is inexpensive to produce and so disposable after one use only.

SUMMARY OF THE INVENTION

The present invention relates to an endoscopic biopsy device, the biopsy device including two individual members or "jaws" which are pivoted about a common axis thereby forming a forceps, each jaw including a tissue capturing means, such as a biopsy cup having a concave body, and an actuator member, the actuator member attaching to a jaw at a flexible joint.

In one embodiment each actuator member is preferably connected, at the end distal the biopsy cups, to operating means such as an endoscope cable, which can be manipulated by a doctor performing the biopsy. Manipulation of the operating means transmits forces to the actuator members which causes movement of the actuator members which in turn leads to flexion or extension of the flexible joint members causing the biopsy cups to move between their open and closed positions.

In a still further embodiment the biopsy head is formed from a synthetic plastics material such as polyamide nylon.

In a preferred embodiment, the individual members are held together relative one another at the pivotal point by means of a pin or a screw made from a suitable plastics or any other material and adapted such that the biopsy heads can articulate relative one another upon actuation.

Preferably there is a space between the biopsy cups at the end closest the pivotal point, the space allowing the escape of fluids or excess tissue from between the cups. If the space is not provided an air lock may result preventing a sufficient amount of tissue for sampling from being caught between the cups. There may also be cases in which the biopsy cups are prevented from closing due to tissue being caught between the cups on the side opposite to the opposed cutting surface.

Consequently. according to the present invention there is provided a biopsy device comprising:

a pair of biopsy jaws, each of said jaws having a tissue capturing means at a first end and a flexible joint at a second end, pivot engagement means being located between said first and second ends;

a pair of actuator members each coupled to one of said joints;

an actuator housing surrounding said actuator members;

a pivot means interconnecting said actuator housing and said pair of saws;

each said biopsy jaw, including said flexible joint, being formed integrally with said actuator member.

According to a further aspect of the invention there is provided a biopsy jaw forming one half of a pair of forceps for use in a biopsy device, said jaw including a flexible joint integrally connected to an actuator member.

It will be realised that, because each of the biopsy jaws, including tissue capturing means such as a cup, are attached to the actuator member by way of a flexible joint member, there is no requirement for the individual components to be hingedly connected. This has the advantage that each jaw, including a hinge, can be formed integrally with an actuator member, the moulded individual members are identical and can be pinned together at the pivotal point such that the edges of the biopsy cups may be brought into cutting opposition. The fact that the individual members can be moulded in one piece results in decreased production costs making it feasible to use the biopsy heads for only one procedure on a patient before their disposal.

BRIEF DESCRIPTION OF THE DRAWINGS

FIG. 3 is a side elevational view of a biopsy head according to the present invention with the biopsy cups in a closed position.

FIG. 4 is a side elevational view of the biopsy head of FIG. 3 with the biopsy cups in an open position.

FIG. 5 is a view of an endoscopy device incorporating a biopsy head according to the present invention.

BEST MODE OF CARRYING OUT THE INVENTION

The following description is given by way of example only of one preferred embodiment of the invention.

Figure 1:
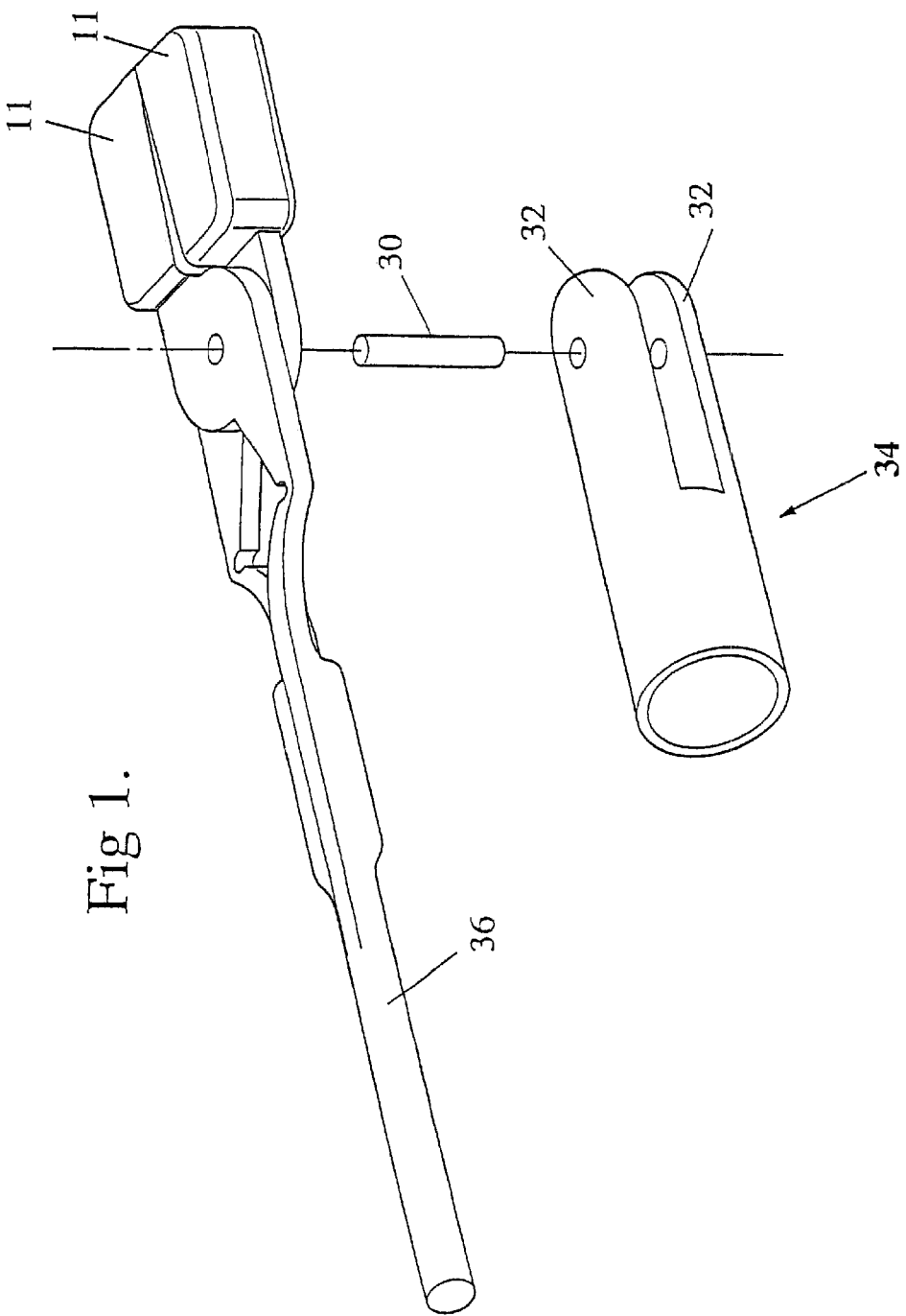
FIG. 1 is a view of the components of a biopsy head according to the present invention when disassembled.

With reference to FIG. 1, which shows a disassembled biopsy device or "head" according to the present invention, it is seen that there are provide two identical individual members 11 each being a "jaw" of the biopsy head.

Figure 2:
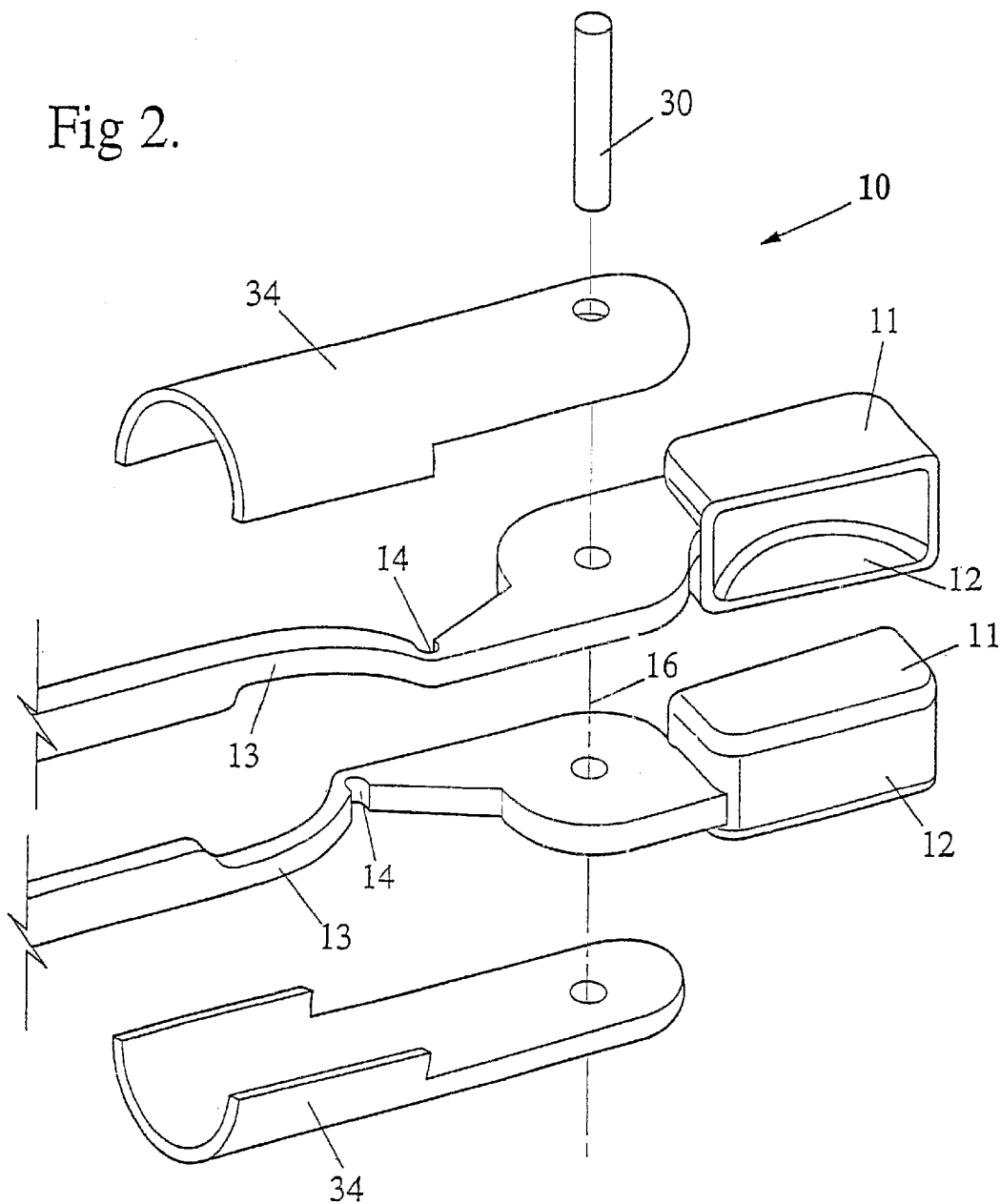
FIG. 2 is an exploded view of a biopsy head according to the present invention with components orientated in the positions they assume when assembled.

When assembled, jaws 11 are pivotally connected by pin 30 between flanges 32 of actuator housing 34. Pin 30 is kept in place, for example, by heat welding it at each end to actuator housing 34. With reference to FIG. 2, which is an exploded view of the biopsy head when assembled, it is seen that jaws 11 are virtually identical individual members. Each jaw 11 includes a biopsy cup 12 connected to an actuator member 13. Each actuator member 13 has a notch between its ends which forms an integral flexible joint 14 and is housed within actuator housing 34. The individual members 11 are pivotable, by means of pin 30, about a common axis 16. The individual members 11 are positioned on opposite sides of a vertical plane 15 which passes between the jaws 11 and through the axis 16. See FIG. 3. As also is shown in FIG. 3, the flexible joints 14 are displaced in opposite directions from the plane 15, and the jaw and the joint associated therewith are on opposite sides of the plane.

It has been found that actuator jaws 11 and pivot pin 30 may be conveniently made from a polyamide nylon although other types of nylon and synthetic materials would also be appropriate. The housing 34 is preferably made of polycarbonate or some synthetic material harder than nylon, or even of metal, in order that it support pivot pin 30 without undue deformation. Significantly, it is most convenient to form each jaw 11 and actuator 13 in a single die injection or moulding process. It will be noted that flexible joints 14 are formed without recourse to the hinge structures which are present in prior art biopsy heads.

A user of biopsy head 10 is able to manipulate actuator members 13 relative to actuator housing 34 in such manner that the integral flexible joints 14 flex. Flexing of both joints 14, by applying a pushing force on actuator members 13 towards pivot axis 16, results in articulation of the biopsy cups 12 away from each other and into an open configuration. This product is clear from FIGS. 3 and 4.

The user can further manipulate members 13 by applying on them a pulling force in a direction away from pivot axis 16 whereupon the joints 14 extend which moves the biopsy cups 12 to the closed position.

Each biopsy cup 12, which operates as a tissue capturing means, has a concave body 17 that has a free edge 18. Free edges 18 are adapted to abut against one another, at least at end 19 of the biopsy cups 12 distal pivotal point 16 when the biopsy head is in the closed position as depicted in FIG. 3.

The abutting edges 18 are sufficiently rigid and sharp that in use a small sample of tissue can be cut from the underlying tissue when caught between the edges 18.

The edges 18 should lie in sufficient proximity around the periphery of the biopsy cups 12 when they are in the closed position such that stray tissue will not find its way into the biopsy cups 12 as the biopsy head 10 is placed into the body of a patient or withdrawn from it. Similarly, the biopsy cups 12 must reliably retain a sample obtained within them. There is however a space 21 formed between the biopsy cups 12 adjacent the end of the biopsy cups 12 closest to the pivotal point 16. Space 21 allows excess tissue to protrude from between from the biopsy cups 12 as the biopsy head 10 is closed around a tissue sample.

Actuator members 13 are connected to a suitable operating cable 36 shown in FIG. 1. In the past cable 36 has typically comprised a metallic wire. However the present invention optionally allows for the formation of an extruded plastic cable integral with actuator member 13. Cable 36 is sufficiently long to span internally the length of an endoscope tube 38 wherein it is connected to a conventional operating trigger 40. Endoscope tube 38 is connected to one end to actuator housing 34 of the biopsy head and at the other to handle 42. Accordingly by pushing operating trigger 40 cable 36 is pushed towards pivot pin 30 and jaws 11 assume the configuration shown in FIG. 4.

In use, biopsy head 10 is positioned adjacent the tissue to be sampled and the jaws opened as described. Cable 36 is then drawn backwards by the operating device causing biopsy cups 12 to reverse their previous movement and come together.

Any tissue caught between biopsy cups 12 will be sheared from the surrounding tissue by edges 18 as they are brought together.

The endoscope can then be withdrawn from the patient and the tissue sample recovered from the biopsy cups 12.

It will be appreciated by persons skilled in the art that numerous variations and/or modifications may be made to the invention as shown in the specific embodiments without departing from the spirit or scope of the invention as broadly described. The present embodiments are, therefore, to be considered in all aspects as illustrative and not restrictive.

What is claimed is:

1. A biopsy device comprising a pair of jaws each having tissue capturing means; a first actuating arm constituting an integral and unitary part of one of the jaws; a second actuating arm constituting an integral and unitary part of the other of the jaws, each said actuating arm including an integral, unitary flexible joint; pivot means coupling said jaws to one another for conjoint pivotal movements of said jaws between open and closed positions about a common axis positioned between the respective jaws and flexible joints, the flexible joint of one said actuating arm being displaced laterally from said axis in one direction and the flexible joint of the other said actuating arm being displaced laterally from said axis in a direction opposite said one direction; and operating means coupled to each said actuating arm and operable to transmit forces via said flexible joints to said actuating arms and effect simultaneous pivotal movements thereof about said axis between said positions.

2. The biopsy device according to claim 1 wherein said flexible joints occupy positions on opposite sides of a plane passing between said jaws and through said axis.

3. The biopsy device according to claim 2 wherein said jaws occupy positions on opposite sides of said plane, the positions of each said jaw and the associated flexible joint being on opposite sides of said plane.

4. The biopsy device according to claim 1 wherein each said flexible joint is formed by a notch in the associated actuating arm.

5. The biopsy device according to claim 1 wherein said operating means comprises a cable integral with both of said first and second actuating arms.

6. A biopsy device comprising a pair of jaws pivotally coupled for rocking movements toward and away from one another about an axis, the jaws of said pair of jaws occupying positions on opposite sides of a plane passing between the jaws of said pair of jaws and through said axis; a first actuating arm joined to one jaw of said pair of jaws and including a first integral flexible joint; a second actuating arm joined to the other jaw of said pair of jaws and including a second integral flexible joint, said one jaw and said first flexible joint occupying positions on opposite sides of said plane and said other jaw and said second flexible joint occupying positions on opposite sides of said plane; and operating means coupled to said first and second actuating arms for applying forces thereon in a selected one of two opposite directions, the forces applied on the respective actuating arms being transmitted via their respective flexible joints to the respective jaws for rocking said jaws in a selected one of two opposite directions about said axis.

7. The device according to claim 6 wherein said jaws, said actuating arms, and said joints are molded from plastic material.

8. The device according to claim 7 wherein said plastic material comprises nylon.

9. The biopsy device according to claim 6 wherein said jaws are so configured as to provide a clearance between said jaws proximal said axis when said jaws confront and abut one another.

10. The biopsy device according to claim 6 wherein said operating means is integral with both of said actuating arms.

11. The biopsy device according to claim 10 wherein each of said flexible joints is formed by a notch in the respective actuating arms.

* * * * *